United States Patent [19]
Braden et al.

[11] Patent Number: 5,403,463
[45] Date of Patent: Apr. 4, 1995

[54] ELECTROCHEMICAL SENSOR

[75] Inventors: Christoph Braden, Cologne; Jacques Deprez, Frechen; Holger Ohst, Odenthal; Dirk Pfenning, Leverkusen; Karlheinz Hildenbrand, Krefeld, all of Germany

[73] Assignee: Mannesmann Aktiengesellschaft, Dusseldorf, United Kingdom

[21] Appl. No.: 227,731

[22] Filed: Apr. 14, 1994

[30] Foreign Application Priority Data

Apr. 14, 1993 [DE] Germany ............... 43 12 124.1

[51] Int. Cl.6 ........................................... G01N 27/26
[52] U.S. Cl. ........................... 204/415; 204/431; 204/432; 204/412; 204/283

[58] Field of Search ............. 204/415, 431, 432, 412, 204/283

[56] References Cited

U.S. PATENT DOCUMENTS 4,259,165  3/1981  Miyaka ..................... 204/415

Primary Examiner—John Niebling
Assistant Examiner—Bruce F. Bell
Attorney, Agent, or Firm—Cohen, Pontani, Lieberman, Pavane

[57] ABSTRACT

An electrochemical sensor having at least two electrodes that communicate with a liquid measurement cell electrolyte and a housing that encloses the electrodes and the electrolyte. The surfaces of the electrodes facing the electrolyte bridge web connecting the electrodes are covered with a semipermeable membrane.

8 Claims, 1 Drawing Sheet

ELECTROCHEMICAL SENSOR

BACKGROUND OF THE INVENTION

1. Field of the Invention

The invention is directed to an electrochemical sensor having at least two electrodes communicating with a liquid measurement cell electrolyte within a housing enclosing the electrodes and the electrolyte. Electrochemical sensors are often used as gas detecting devices and as alarm devices. Solid electrolytes are frequently used as electrolytes (for example, see WO 91/16624). However, there are also a number of gas components which can only be measured by electrochemical sensors based on liquid and viscous-liquid measurement cell electrolytes.

2. Description of the Prior Art

In electrochemical sensors of the above-mentioned type, the electrolyte does not completely fill the interior of the sensor housing, since an easily compressible residual gas volume (air cushion) must remain in the measurement cell in order to compensate for alternating external pressures. Loss of electrolyte due to evaporation increases with the age of the measurement cell so that the residual gas volume in the sensor gradually increases with continued use of the sensor. In so doing, the residual gas volume is distributed to different locations in the measurement cell depending on the position or attitude of the sensor. For example, in a vertically upright sensor, a working electrode arranged at the top is completely separated from the electrolyte by the residual gas volume and the measurement cell no longer functions. For this reason, so-called electrolyte bridges, which form an electrical connection between the electrodes, are used in electrochemical sensors based on liquid electrolytes. Techniques for implementing such electrolyte bridges employ filter materials which have a sufficient capillary action to ensure the transport of electrolyte through the capillaries of the filter material. A problem is posed in that the electrolyte bridges must be mounted in the interior of the cell so that the majority of the electrolyte bridge is immersed in the electrolyte in every position of the measurement cell. Experience has shown that application of mechanical pressure against the electrolyte bridges to wet the electrodes is unsatisfactory and above all has poor reproducibility.

SUMMARY OF THE INVENTION

Proceeding from this point, it is an object of the present invention to provide electrochemical sensors based on liquid measurement cell electrolytes which an optimal wetting of the electrodes with the electrolyte is ensured in all applications regardless of the geometrical position of the sensor so that the sensor specifications, particularly sensitivity, are entirely independent of the respective geometrical position of the sensor.

Pursuant to this object, and others which will become apparent hereafter, one aspect of the present invention resides in coating the surfaces of the electrodes facing the electrolyte and at least one electrolyte bridge web connecting the electrodes are coated with a semipermeable membrane.

The electrolyte bridge web is preferably formed by a membrane sheet applied to the inside of the housing, and the previously conventional bridge web between the electrodes can be dispensed with.

The coating of the inside of the housing and electrodes can be effected in principle with finished, commercially available membranes. However, the coating is preferably effected by means of in-situ production of the membrane using the so-called phase inversion method. The fundamentals of this method are known and described, for example, in "Microfiltration with Membranes", S. Ripperger, VCH 1992. Starting with polymer solutions (casting solutions) which are applied to a substrate with a wet thickness in the range of 50 to 500 $\mu$m, the membrane formation process call be effected by a) steaming or evaporating a portion of the solvent or solvent component,
b) by a change in temperature, or
c) by addition of a further component (precipitation coagulation, preferably in water).

The polymers used for producing the membrane and their solvents used for producing the casting solution are also known. Some examples of common membrane polymers are cellulose esters, polyamides, polysulfones, fluoropolymerizates, polyacrylonitriles, polyimides and polyolefins. Other suitable membrane polymers are, e.g., polyetherketones, polysulfones with cycloaliphatic diol components and polyhydantoins (see DE 2 431 071) which, apart from their pH stability in a highly acidic milieu, are relatively highly hydrophilic. For this reason, polyhydantoin membranes are particularly well-suited for the membrane-coated electrochemical electrodes according to the invention.

Developments for the production of hydrophilized membranes based on hydrophobic polymers such as polyvinylidene fluoride or polysulfone and polyethersulfone which are characterized by a particularly good stability with respect to chemicals and pH are also known. Some examples are:

blends of polyvinylidene fluoride or polysulfone with polyvinylpyrrolidone, and hydrophilic coating of the internal structure, grafting a hydrophilic molecule part on existing skeletal polymers, e.g. by plasma or corona treatment.

Membranes with high proportions of solids are particularly advantageous. Thus, especially advantageous results can be achieved with membrane coats consisting of approximately 85 parts titanium dioxide and 15 parts polysulfone. In parallel examples, the polysulfone was replaced with the more hydrophilic polyhydantoin (Bayer AG). The sensors coated with the corresponding $TiO_2$-containing polyhydantoin membranes also showed excellent test results and were distinguished by very good wetting with the electrolyte liquid. In addition to titanium dioxide which is added to the polymer casting solution, other fillers such as zinc oxide, talc, barium sulfate, zeolite, bentonite, calcium carbonate, silica gel, Aerosile (Degussa Company) or microcrystalline cellulose can also be considered. These fillers can either remain untreated or can be chemically modified on the surface, e.g. hydrophilized.

The invention provides numerous advantages, including a substantially greater operating reliability due to the membrane coating. Additionally, the membrane coats which adhere well to the electrode surfaces always ensure good wetting due to their capillarity and hydrophilic character.

Accordingly, it was possible to eliminate the error commonly observed in the past, i.e. that the measuring sensitivity of the sensor and accordingly the indication of the device depended on the spatial attitude and position of the device.

By constructing the sensor so that the inner surfaces of the housing are coated by a semipermeable membrane, the difficulty of mounting the electrolyte bridges is eliminated. In comparison, the membrane coating call be applied economically with respect to manufacturing technique. A complete wetting of the electrodes with long-term stability is brought about by the hydrophilic membrane layer.

The complete lining of the inner surface of the housing with a hydrophilic membrane coat ensures a permanent and stable electrochemical connection of the electrodes coated with the same membrane material regardless of the position of the sensor.

The membrane coating also prevents leakage in the housing wall of the sensor and accordingly prevents the electrolyte from escaping. In previous conventional measurement cells such leakage resulted in a total failure of the device, frequently in conjunction with irreparable corrosion of and damage to the measurement electronics for evaluating the sensor signals.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PREFERRED EMBODIMENTS

Figure 1:
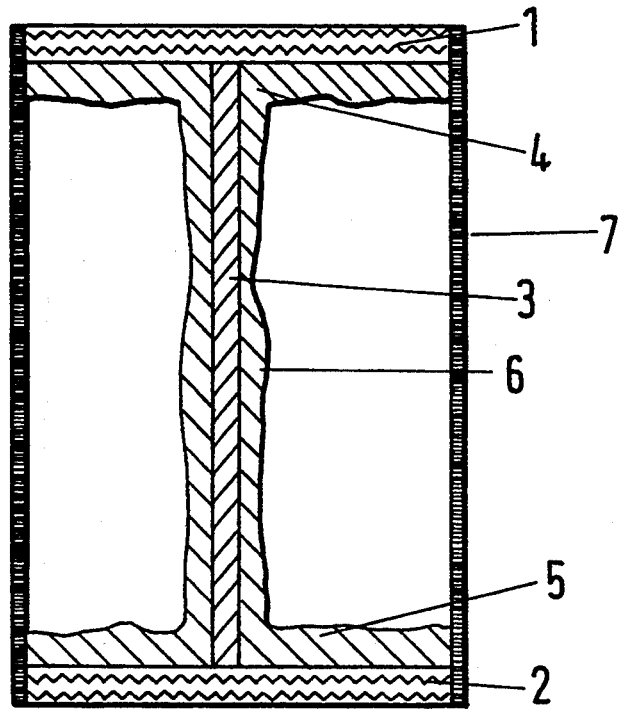
FIG. 1 shows an electrochemical two-electrode sensor with an electrolyte bridge web connecting the electrodes.

The electrochemical sensor shown schematically in FIG. 1 substantially includes a working electrode 1 and a counter-electrode 2 which are electrically connected via an electrolyte bridge web 3. The bridge web 3 is made of an absorbent material, such as filter paper, which is saturated with a measurement cell electrolyte, e.g. $H_2SO_4$. The inner surfaces of the electrodes 1, 2 facing the electrolyte are provided with titanium dioxide-containing membrane coats 4, 5 that have a thickness of approximately 500 $\mu$m. Like the inner surfaces of the electrodes, the electrolyte bridge web 3 is also coated with a titanium dioxide-containing membrane 6. The membrane coating 4, 5, 6 is effected according to the previously discussed phase inversion method, wherein the variants of the selective solvent evaporation and the precipitation coagulation are preferably effected in water. All structural component parts of the sensor are accommodated in a housing 7.

Figure 2:
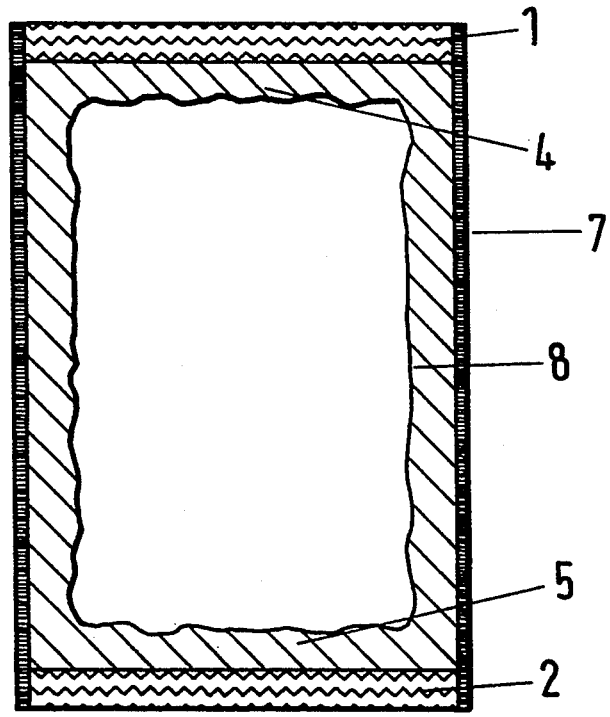
FIG. 2 shows an electrochemical two-electrode sensor in which the inner surfaces of the housing are provided with a membrane coat.

The electrochemical sensor shown schematically in FIG. 2 is constructed exactly like the sensor according to FIG. 1 with respect to the electrodes 1, 2. However, in contrast to the sensor described above, the electrolyte bridge web 3 in this case is formed by a membrane film 8 applied-to the inside of the housing 7. The electrodes 1, 2 are coated with a membrane film 4, 5 as in the construction according to FIG. 1. The membrane film 8 lining the entire inner wall of the housing 7 thus assumes the function of the electrolyte bridge web 3. As a result of the outstanding wetting characteristics of the hydrophilized membrane film, the electrode surfaces and the inner walls of the housing 7 are completely wetted by electrolyte. Since all inner sides of the measurement cell are coated by the hydrophilic membrane, the connection with the electrolyte reservoir is always ensured regardless of the geometric position of the measurement cell. The electrochemical contact between the electrodes via the conductive coating with the electrolytes contained therein can therefore never be interrupted.

Embodiment Example

A porous Teflon sheet coated with platinum black serves as a supporting membrane.

A. Production of the polymer casting solution ($TiO_2$-containing polyhydantoin solution)

89.7 g polyhydantoin (hydantoin sheets, Bayer AG) were dissolved in 40-percent 0 [sic] g N-methylpyrrolidone (NMP) by stirring. 508.3 g titanium dioxide were dispersed in this polymer solution with a high-speed agitator. This filler-containing casting solution was then degasified in a vacuum.

B. Membrane Coating

The filler-containing polymer casting solution from A was applied with an applicator to the Teflon sheet (substrate) coated with platinum black with a wet thickness of 250 $\mu$m, coagulated in water and then washed with clean water and dried.

The invention is not limited by the embodiments described above which are presented as examples only but can be modified in various ways within the scope of protection defined by the appended patent claims.

I claim:

1. An electrochemical sensor, comprising: a housing; a liquid measurement cell electrolyte arranged in the housing; two electrodes arranged in the housing to communicate with the liquid measurement cell electrolyte, the electrodes having surfaces that face the electrolyte; at least one electrolyte bridge web that connects the electrodes; and a semipermeable membrane coat provided to cover the surfaces of the electrodes that face the electrolyte and at least one electrolyte bridge web.

2. An electrochemical sensor according to claim 1, wherein the electrolyte bridge web is formed by a hydrophilized membrane film applied to the inside of the housing, the hydrophilized membrane film is one selected from the group consisting of polysulfone, polyvinylidene fluoride, polyamide and polyhydantoin.

3. An electrochemical sensor according to claim 2, wherein the hydrophilized membrane film forms the semipermeable membrane coat.

4. An electrochemical sensor according to claim 2, wherein the hydrophilized semipermeable membrane is made of a filler-containing membrane material that has a filler content that is 85 to 75 parts and a polymer content that is 15 to 25 parts.

5. An electrochemical sensor according to claim 1, wherein the semipermeable membrane coat contains 15 to 25 parts polysulfone and 85 to 75 parts titanium dioxide, the membrane coat having a thickness of 25 $\mu$m to 700 $\mu$m.

6. An electrochemical sensor according to claim 5, wherein the membrane coat has a thickness of 100 $\mu$m to 500 $\mu$m.

7. An electrochemical sensor according to claim 1, wherein the semipermeable membrane contains 15 to 25 parts polyhydantoin and 85 to 75 parts titanium dioxide, the membrane having a thickness of 25 $\mu$m to 700 $\mu$m.

8. An electrochemical sensor according to claim 7, wherein the membrane has a thickness of 100 $\mu$m to 500 $\mu$m.

* * * * *